(12) United States Patent
Sowelam et al.

(10) Patent No.: US 7,203,541 B2
(45) Date of Patent: Apr. 10, 2007

(54) REAL-TIME OPTIMIZATION OF RIGHT TO LEFT VENTRICULAR TIMING SEQUENCE IN BI-VENTRICULAR PACING OF HEART FAILURE PATIENTS

(75) Inventors: Sameh Sowelam, Maple Grove, MN (US); Todd J. Sheldon, North Oaks, MN (US); Yong K. Cho, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 447 days.

(21) Appl. No.: 10/799,260

(22) Filed: Mar. 12, 2004

(65) Prior Publication Data

US 2005/0203579 A1 Sep. 15, 2005

(51) Int. Cl.
*A61N 1/368* (2006.01)
*A61N 1/365* (2006.01)

(52) U.S. Cl. ............... 607/19; 607/9; 607/18
(58) Field of Classification Search ............ None
See application file for complete search history.

(56) References Cited

U.S. PATENT DOCUMENTS

| | | | |
|---|---|---|---|
| 5,261,418 A | 11/1993 | Ferek-Petric | |
| 5,334,222 A | 8/1994 | Salo et al. | |
| 5,454,838 A | 10/1995 | Vallana et al. | |
| 5,540,727 A | 7/1996 | Tockman et al. | |
| 5,549,650 A | 8/1996 | Bornzin et al. | |
| 5,549,652 A * | 8/1996 | McClure et al. ............ 607/28 |
| 5,626,623 A | 5/1997 | Kieval et al. | |
| 5,628,777 A | 5/1997 | Moberg et al. | |
| 5,693,075 A | 12/1997 | Plicchi et al. | |
| 5,700,283 A | 12/1997 | Salo | |
| 5,836,987 A | 11/1998 | Baumann et al. | |
| 6,070,101 A | 5/2000 | Struble et al. | |
| 6,077,236 A | 6/2000 | Cunningham | |
| 6,223,082 B1 | 4/2001 | Bakels et al. | |
| 6,473,645 B1 | 10/2002 | Levine | |
| 6,477,406 B1 | 11/2002 | Turcott | |
| 6,795,732 B2 * | 9/2004 | Stadler et al. ............ 607/17 |
| 7,092,759 B2 * | 8/2006 | Nehls et al. ............. 607/19 |
| 7,142,919 B2 * | 11/2006 | Hine et al. ............... 607/17 |
| 2002/0049478 A1 | 4/2002 | Ding et al. | |
| 2004/0049112 A1 | 3/2004 | Yu et al. | |
| 2004/0220631 A1 * | 11/2004 | Burnes et al. ............ 607/9 |
| 2004/0225332 A1 * | 11/2004 | Gebhardt et al. ......... 607/17 |
| 2004/0260346 A1 * | 12/2004 | Overall et al. ............ 607/4 |
| 2005/0027320 A1 * | 2/2005 | Nehls et al. ............. 607/9 |

* cited by examiner

*Primary Examiner*—Carl Layno
(74) *Attorney, Agent, or Firm*—Paul H. McDowall; Girma Wolde-Michael (57) ABSTRACT

A system and automated method for assessing ventricular synchrony in ambulatory patients is provided including at least one mechanical sensor (e.g., accelerometer, tensiometric sensor, force transducer, and the like) operatively coupled to a first myocardial location in order to measure a wall motion signal of a first chamber, and a second mechanical sensor operatively coupled to a second myocardial location in order to measure a wall motion signal of a second chamber. The wall motion signals are processed in order to identify the time at which a fiducial (e.g., an inflection point, a threshold crossing, a maximum amplitude, etc.) occurs for each respective signal. The temporal separation between the fiducial points on each respective signal is measured as a metric of ventricular synchrony and can be optionally utilized to adjust pacing therapy timing to improve synchrony.

42 Claims, 6 Drawing Sheets

REAL-TIME OPTIMIZATION OF RIGHT TO LEFT VENTRICULAR TIMING SEQUENCE IN BI-VENTRICULAR PACING OF HEART FAILURE PATIENTS

FIELD OF THE INVENTION

The present invention relates generally to implantable cardiac monitoring devices and more particularly to cardiac monitoring systems including at least two cardiac wall motion sensors (e.g., tensiometric sensors, accelerometer sensors, and the like) and associated methods for measuring cardiac wall motion to assess ventricular synchrony.

BACKGROUND OF THE INVENTION

Evaluation of ventricular synchrony is of interest for both diagnostic and therapeutic applications. During normal cardiac function the cardiac chambers observe consistent time-dependent relationships during the systolic (contractile) phase and the diastolic (relaxation) phase of the cardiac cycle. During cardiac dysfunction associated with pathological conditions or following cardiac-related surgical procedures, these time-dependent mechanical relationships are often altered. This alteration, when combined with the effects of weakened cardiac muscles, reduces the ability of the ventricles to generate contractile strength resulting in hemodynamic insufficiency.

Ventricular dyssynchrony following coronary artery bypass graft (CABG) surgery is a problem encountered relatively often, requiring post-operative temporary pacing. Atrio-biventricular pacing has been found to improve post-operative hemodynamics following such procedures. A widely accepted, standardized method for selecting pacing sites and pacing intervals that provide the greatest hemodynamic benefit to the patient during the critical recovery phase, however, has not been available.

Chronic cardiac resynchronization therapy (CRT) has been clinically demonstrated to improve indices of cardiac function in patients suffering from congestive heart failure. Cardiac pacing may be applied to one or both ventricles or multiple heart chambers, including one or both atria, to improve cardiac chamber coordination, which in turn is thought to improve stroke volume and pumping efficiency. Clinical follow-up of patients undergoing resynchronization therapy has shown improvements in hemodynamic measures of cardiac function, left ventricular volumes, and wall motion. However, not all patients respond favorably to cardiac resynchronization therapy. Physicians are challenged in selecting patients that will benefit and in selecting the optimal pacing intervals between the atria and ventricles (A-V intervals) and between the ventricles (V-V intervals), also collectively referred to herein as "A-V-V" intervals, applied to resynchronize the heart chamber contractions.

Selection of pacing intervals may be based on echocardiographic studies performed to determine the settings resulting in the best net output, or other selected hemodynamic response. In the InSync III clinical trial conducted to evaluate resynchronization therapy, the A-V-V intervals were optimized individually in patients by shortening the A-V interval to maximize LV filling without truncating the atrial contribution as observed by echocardiography and to maximize stroke volume. Acute increases in stroke volume have been related to chronically sustained clinical benefits.

Echocardiographic approaches for optimizing resynchronization therapy provide only an open-loop method for selecting pacing intervals. After evaluating the hemodynamic effect of varying combinations of pacing intervals, a clinician must manually select and program the desired parameters. Furthermore, an echocardiographic procedure for optimizing resynchronization therapy can require substantial time and personnel. A technician is required to program A-V-V timing schemes while a sonographer interprets the effects on the heart. A period of hemodynamic stabilization is generally desired prior to evaluating the hemodynamic effects of a particular timing scheme. However, the time required to reach hemodynamic stability may be uncertain. Echocardiographic assessments of ventricular synchrony or the hemodynamic response to resynchronization therapy are further limited, therefore, in that measurements are available only at a particular time point and may be affected by the patient's condition on that particular day.

Numerous algorithms for optimizing the A-V interval during dual chamber pacing to improve cardiac function or hemodynamic status have been described including automatic algorithms based on an implantable sensor of hemodynamic function. Reference is made, for example, to U.S. Pat. No. 5,700,283 to Salo; and U.S. Pat. No. 5,626,623 issued to Kieval et al. Examples of implantable sensors proposed or known for measuring hemodynamic function include impedance sensors for measuring cardiac output, intracardiac blood pressure sensors, acoustical sensors for monitoring heart sounds, and Doppler ultrasound sensors for monitoring flow. Reference is made, for example, to U.S. Pat. No. 5,334,222 to Salo et al.; and U.S. Pat. No. 6,477,406 issued to Turcott.

Multichamber pacing systems having automated selection of pacing intervals have also been proposed. A four-chamber pacing system that includes impedance sensing for determining the timing of right heart valve closure or right ventricular contraction and adjusting the timing of delivery of left ventricular pace pulses is generally disclosed in U.S. Pat. No. 6,223,082 issued to Bakels, et al., incorporated herein by reference in its entirety. Programmable coupling intervals selected so as to provide optimal hemodynamic benefit to the patient in an implantable multichamber cardiac stimulation device are generally disclosed in U.S. Pat. No. 6,473,645 issued to Levine, incorporated herein by reference in its entirety. Improvement in cardiac function is based on a generic physiological sensor. Such automated systems have not been put to clinical use to date.

Implantable sensors for monitoring heart wall motion have been described or implemented for use in relation to the right ventricle. A sensor implanted in the heart mass for monitoring heart function by monitoring the momentum or velocity of the heart mass is generally disclosed in U.S. Pat. No. 5,454,838 issued to Vallana et al. A catheter for insertion into the ventricle for monitoring cardiac contractility having an acceleration transducer at or proximate the catheter tip is generally disclosed in U.S. Pat. No. 6,077,236 issued to Cunningham. Implantable leads incorporating accelerometer-based cardiac wall motion sensors are generally disclosed in U.S. Pat. No. 5,628,777 issued to Moberg, et al. A device for sensing natural heart acceleration is generally disclosed in U.S. Pat. No. 5,693,075, issued to Plicchi, et al. A system for myocardial tensiometery including a tensiometric element disposed at a location subject to bending due to cardiac contractions is generally disclosed in U.S. Pat. No. 5,261,418 issued to Ferek-Petric et al. All of the above-cited patents are hereby incorporated herein by reference in their entirety.

Detection of peak endocardial wall motion in the apex of the right ventricle for optimizing A-V intervals has been validated clinically. A system and method for using cardiac wall motion sensor signals to provide hemodynamically optimal values for heart rate and AV interval are generally disclosed in U.S. Pat. No. 5,549,650 issued to Bornzin, et al., incorporated herein by reference in its entirety. A cardiac stimulating system designed to automatically optimize both the pacing mode and one or more pacing cycle parameters in a way that results in optimization of a cardiac performance parameter, including for example heart accelerations, is generally disclosed in U.S. Pat. No. 5,540,727, issued to Tockman, et al.

BRIEF SUMMARY OF THE INVENTION

The present invention is directed toward providing an automated method for assessing ventricular synchrony in ambulatory patients. Such methods may be advantageously put to use in managing therapies delivered by an implantable medical device (IMD) to improve hemodynamic performance in a closed control loop. In one family of inventive embodiments, implantable cardiac monitoring systems and associated methods are provided wherein two or more lead-based accelerometers are deployed within or are coupled to the heart (e.g., epicardial deployment) for monitoring ventricular synchrony. Preferably, at least one accelerometer is positioned in operative relation to the right ventricle in order to measure a right ventricular wall motion signal, and a second accelerometer is positioned in operative relation to the left ventricle in order to measure a left ventricular wall motion signal.

The two or more accelerometer signals are processed in order to identify the time at which an inflection (e.g., fiducial point) occurs on each respective signal. The time differential between the fiducial points on each respective signal is measured as a metric of ventricular synchrony.

In a preferred embodiment, a method for measuring ventricular synchrony includes detecting the R-wave from an EGM signal and defining a sensing window of time relative to the detected R-wave. Raw accelerometer signal segments defined by the sensing window are averaged for a predetermined number of consecutive cardiac cycles. The averaged signal segment for a given accelerometer signal is reversed in time to define a filter template used by a matched filter. A raw accelerometer signal is passed through the matched filter to obtain a processed accelerometer signal having an improved signal-to-noise ratio. A fiducial point on the processed accelerometer signals obtained from each of the accelerometers is identified for a given cardiac cycle. A fiducial point may be, for example, a peak amplitude, peak slope, threshold crossing, or the like. The time difference between the occurrence of the fiducial points on each of the processed accelerometer signals is measured as a metric of ventricular synchrony.

The metric of ventricular synchrony may be redetermined periodically such that trends in ventricular synchrony may be determined. Measured ventricular synchrony metrics may be stored in the memory of an associated implantable device and made available during a device interrogation operation for review by a clinician. Trends in ventricular synchrony may be used for diagnostic purposes, disease assessment, evaluation of therapy response, and optimizing treatments.

The evaluation of ventricular synchrony in accordance with the methods of the present invention may be utilized in a closed-loop method for optimizing a therapy delivered by an IMD. As such, the implantable cardiac monitoring device provided for monitoring ventricular synchrony may further include therapy delivery capabilities such as drug delivery or cardiac resynchronization therapy. In one embodiment, ventricular synchrony metrics or trends are used to optimize cardiac pacing intervals applied during cardiac resynchronization therapy.

The present invention may be realized in an implantable cardiac monitoring system including an implantable device coupled to two or more lead-based accelerometers deployed within a patient's heart and including a sensing electrode for sensing an EGM or ECG signal. The implantable device includes EGM/ECG sensing circuitry for receiving an EGM/ECG signal and detecting R-waves; wall motion sensing circuitry for receiving at least two accelerometer signals and a processing unit embodied in hardware or software for processing the accelerometer signals to determine a ventricular synchrony metric. The implantable device will generally include memory for storing ventricular synchrony metric results and telemetry circuitry for receiving programming and interrogation commands and transmitting stored data to an external device. The implantable device may further include therapy delivery capabilities controlled by a control system, which may utilize ventricular synchrony measurement results in setting therapy delivery parameters.

DETAILED DESCRIPTION OF THE PREFERRED EMBODIMENTS

As indicated above, the present invention is directed toward providing methods and apparatus for monitoring ventricular synchrony in an ambulatory patient using at least a pair of transducers and automatically storing pacing therapy timing information and/or dynamically controlling said pacing therapy timing to maintain ventricular synchrony. A ventricular synchrony metric determined in accordance with the present invention is useful for optimizing inter-ventricular pacing intervals during chronic resynchronization therapy (CRT) delivery for treating heart failure or for managing other cardiac therapies such as medical therapies. As such, the present invention may be embodied in an implantable medical device (IMD) having ventricular synchrony monitoring capabilities and may further include CRT delivery capabilities.

While the benefits of the present invention are expected to be particularly advantageous when put to use in a fully IMD system, aspects of the present invention may also be beneficial when practiced in conjunction with external devices such as temporary pacemakers used to restore ventricular synchrony following coronary arterial bypass graft (CABG) surgical procedures. Therefore, methods described herein are not limited to use with implantable systems, however, for the sake of illustration the present invention will be described in the context of an IMD system.

Figure 1:
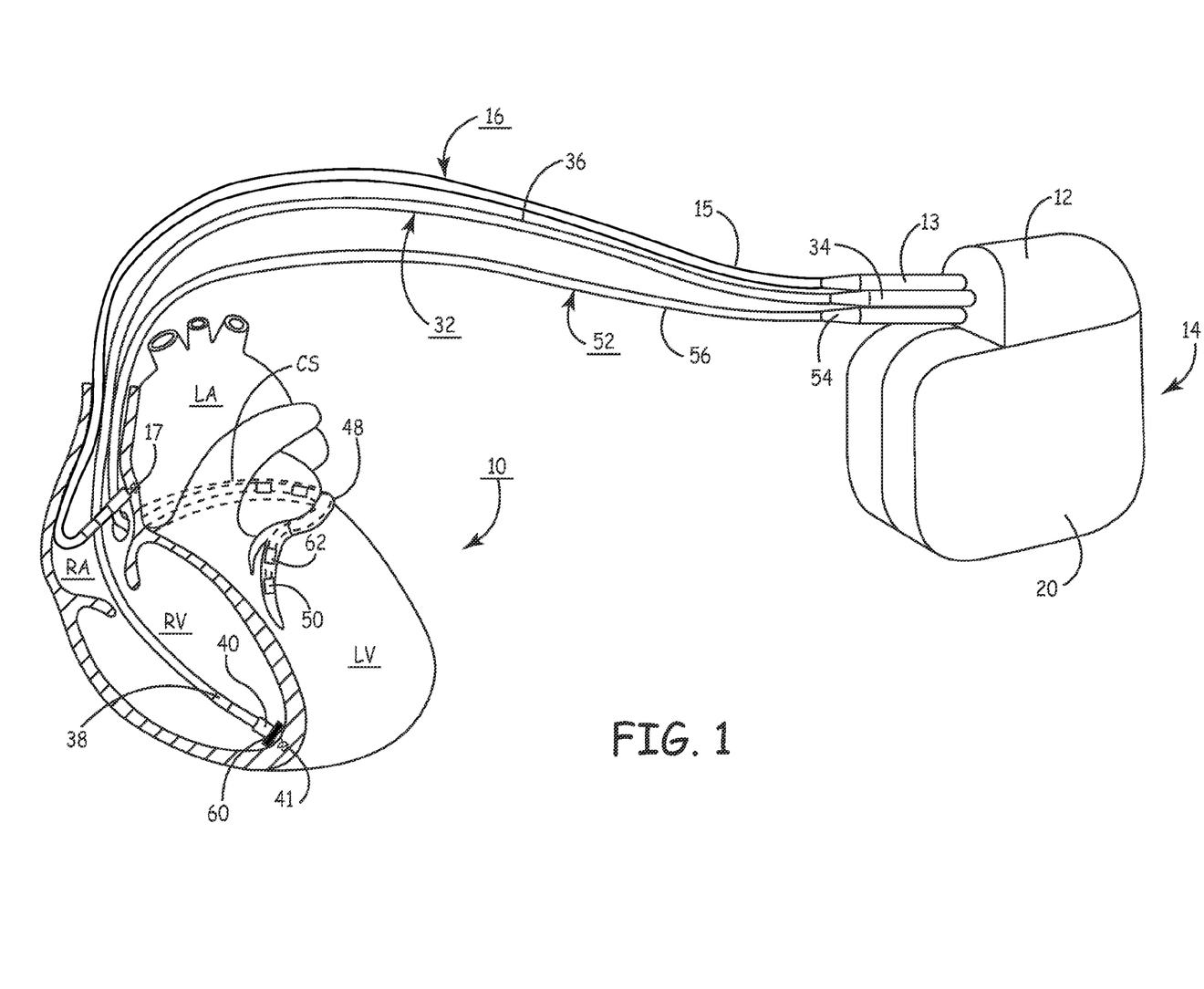
FIG. 1 depicts an IMD in which the present invention may be implemented.

FIG. 1 depicts an IMD in which the present invention may be implemented. The IMD 14 is embodied as a multi-chamber cardiac pacemaker or implantable pulse generator (IPG). The multi-chamber IPG 14 is provided for restoring ventricular synchrony by delivering pacing pulses to one or more heart chambers as needed to control the heart activation sequence. The IPG 14 is shown in communication with patient's heart 10 by way of three leads 16, 32 and 52. The heart 10 is shown in a partially cut-away view illustrating the upper heart chambers, the right atrium (RA) and left atrium (LA), and the lower heart chambers, the right ventricle (RV) and left ventricle (LV), and the coronary sinus (CS) extending from the opening in the right atrium laterally around the atria to form the great cardiac vein 48, which branches to form inferior cardiac veins.

The IPG 14 is implanted subcutaneously in a patient's body between the skin and the ribs. Three transvenous endocardial leads 16, 32 and 52 connect the IPG 14 with the RA, the RV and the LV, respectively. Each lead has at least one electrical conductor and pace/sense electrode. A remote indifferent can electrode 20 is formed as part of the outer surface of the housing of the IPG 14. The pace/sense electrodes and the remote indifferent can electrode 20 can be selectively employed to provide a number of unipolar and bipolar pace/sense electrode combinations for pacing and sensing functions.

The depicted bipolar endocardial RA lead 16 is passed through a vein into the RA chamber of the heart 10, and the distal end of the RA lead 16 is attached to the RA wall by an attachment mechanism 17. The bipolar endocardial RA lead 16 is formed with an in-line connector 13 fitting into a bipolar bore of connector block 12 that is coupled to a pair of electrically insulated conductors within lead body 15 and connected with distal tip RA pace/sense electrode 19 and proximal ring RA pace/sense electrode 21 provided for achieving RA pacing and sensing of RA electrogram (EGM) signals.

Bipolar, endocardial RV lead 32 is passed through the RA into the RV where its distal ring and tip RV pace/sense electrodes 38 and 40 are fixed in place in the apex by a conventional distal attachment mechanism 41. The RV lead 32 is formed with an in-line connector 34 fitting into a bipolar bore of connector block 12 that is coupled to a pair of electrically insulated conductors within lead body 36 and connected with distal tip RV pace/sense electrode 40 and proximal ring RV pace/sense electrode 38 provided for RV pacing and sensing of RV EGM signals. RV lead 32 further includes an RV wall motion sensor 60. RV wall motion sensor 60 may be positioned into or proximate the RV apex for detecting motion or acceleration of the RV apical region. Implantation of an acceleration sensor in the right ventricle is generally disclosed in U.S. Pat. No. 5,693,075 issued to Plicchi, et al., incorporated herein by reference in its entirety.

In this illustrated embodiment, a unipolar, endocardial LV CS lead 52 is passed through the RA, into the CS and further into a cardiac vein to extend the distal LV CS pace/sense electrode 50 alongside the LV chamber to achieve LV pacing and sensing of LV EGM signals. The LV CS lead 52 is coupled at the proximal end connector 54 fitting into a bore of connector block 12. A small diameter unipolar lead body 56 is selected in order to lodge the distal LV CS pace/sense electrode 50 deeply in a cardiac vein branching from the great cardiac vein 48.

Coronary sinus lead 52 is provided with a wall motion sensor 62 capable of generating a signal proportional to the acceleration of the left ventricular free wall. Sensors 62 and 60 are preferably embodied as uniaxial, biaxial, or triaxial sensors (e.g., accelerometers). In particular, sensor 62 is preferably contained in a capsule of a relatively small size and diameter such that it may be included in a coronary sinus lead without substantially increasing the lead diameter or impairing the ability to steer the lead to a left ventricular pacing and sensing site. Sensors 60 and 62 may alternatively be provided as another type of sensor such as an optical sensor, acoustical sensor or a sensor having piezoelectric, inductive, capacitive, resistive, or other elements which directly or indirectly produce a variable signal proportional to myocardial wall acceleration, velocity, displacement or force (including sensors that sense variations in the foregoing). Capacitive diaphragmatic-type sensors, cantilevered-type sensors, impedance-injection sensing circuits, and the like can all be utilized according to the present invention provided they are rendered of biocompatible material and sufficiently robust to withstand the dynamic forces, chemical forces, and macrophage response from phagocytes and the like. With respect to impedance-injection sensing circuits, a substantially continuously injected signal having appropriate frequency and inter-electrode sensing vector can be utilized to detect motion of at least one of the LV and RV. However, for consistency of the text hereof the foregoing sensors and transducer will be chiefly referred to as an accelerometer sensor, with the understanding that all suitable sensors for transducing cardiac wall motion are covered hereby. Furthermore, although the lead 52 is described herein primarily as being deployed through at least a portion of the great cardiac vein, lead 52 can also represent an epicardial lead adapted to couple to any appropriate or suitable location on a portion of the epicardium of the LV chamber.

Sensor 62 is preferably located on CS lead 52 such that when CS lead 52 is positioned for LV pacing and sensing, sensor 62 is located approximately over the left ventricular free wall mid-lateral to mid-basal segments. However, the depicted positions of the leads and electrodes shown in FIG. 1 in or about the right and left heart chambers are approximate and merely exemplary. For example, a left ventricular wall motion sensor 62 may alternatively be located on CS lead 52 such that sensor 62 is positioned in the coronary sinus, in the great cardiac vein, or in any accessible inferior cardiac vein. Furthermore, it is recognized that alternative leads and pace/sense electrodes that are adapted for placement at pacing or sensing sites on or in or relative to the RA, LA, RV and LV may be used in conjunction with the present invention.

In a four chamber embodiment, LV CS lead 52 could bear a proximal LA CS pace/sense electrode positioned along the lead body to lie in the larger diameter coronary sinus adjacent the LA for use in pacing the LA or sensing LA EGM signals. In that case, the lead body 56 would encase an insulated lead conductor extending proximally from the more proximal LA CS pace/sense electrode(s) and terminating in a bipolar connector 54.

In one embodiment of the present invention, and as shown in FIG. 1, one accelerometer is positioned relative to the right ventricle for measuring right ventricular wall motion and a second accelerometer is positioned relative to the left ventricle for measuring left ventricular wall motion. As will be described in greater detail below, signals from a right ventricular accelerometer and signals from a left ventricular accelerometer may be processed and analyzed to obtain a metric of synchrony between the right an left ventricles. Placement of accelerometers or other types of wall motion sensors relative to the right ventricle and left ventricle are not limited to the positions shown in FIG. 1 however and could alternatively be positioned at other right and left ventricular locations using transvenous or epicardial lead-based accelerometers.

Furthermore, the present invention may be practiced with multiple accelerometers positioned at more than one site in the right and/or left ventricle. The methods taught herein for measuring ventricular synchrony may be applied to measuring the synchrony of wall motion between multiple sites in the right and left ventricles and may also be used for measuring the synchrony between multiple sites within one ventricle. Thus inter-ventricular synchrony as well as intra-ventricular synchrony may be assessed using multiple accelerometers or other wall motion sensors and the methods to be described below.

Figure 2:
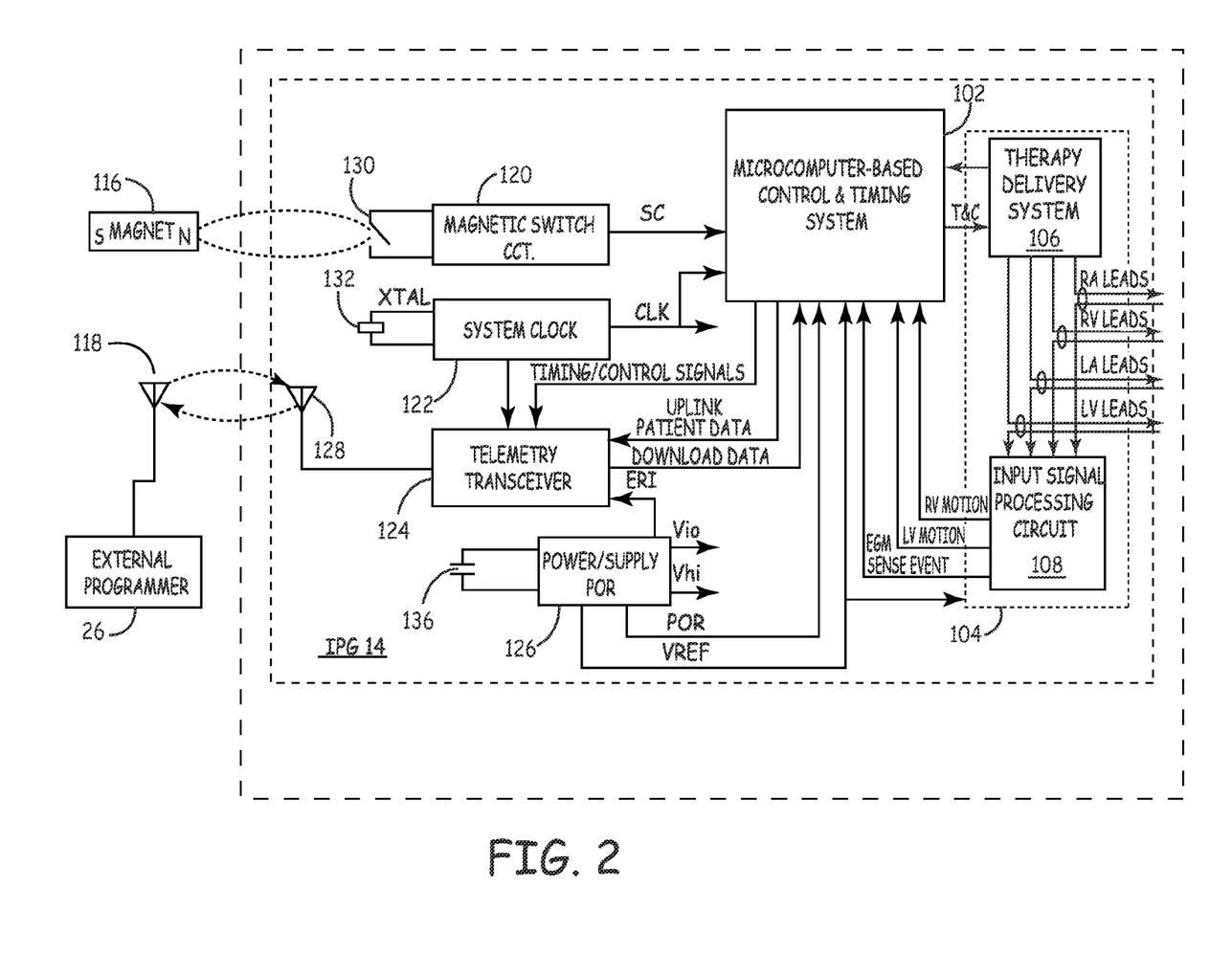
FIG. 2 is a schematic block diagram of an exemplary multi-chamber pacemaker or implantable pulse generator (IPG), such as that shown in FIG. 1, that provides delivery of a resynchronization therapy and is capable of automatically monitoring ventricular synchrony in accordance with the present invention.

FIG. 2 is a schematic block diagram of an exemplary multi-chamber IPG 14, such as that shown in FIG. 1, that provides delivery of a resynchronization therapy and is capable of automatically monitoring ventricular synchrony in accordance with the present invention. The IPG 14 is preferably a microprocessor-based device. Accordingly, microprocessor-based control and timing system 102, which varies in sophistication and complexity depending upon the type and functional features incorporated therein, controls the functions of IPG 14 by executing firmware and programmed software algorithms stored in associated RAM and ROM. Control and timing system 102 may also include a watchdog circuit, a DMA controller, a block mover/reader, a CRC calculator, and other specific logic circuitry coupled together by on-chip data bus, address bus, power, clock, and control signal lines in paths or trees in a manner known in the art. It will also be understood that control and timing functions of IPG 14 can be accomplished with dedicated circuit hardware or state machine logic rather than a programmed microcomputer.

The IPG 14 includes interface circuitry 104 for receiving signals from sensors and pace/sense electrodes located at specific sites of the patient's heart chambers and delivering cardiac pacing to control the patient's heart rhythm and resynchronize heart chamber activation. The interface circuitry 104 therefore includes a therapy delivery system 106 intended for delivering cardiac pacing impulses under the control of control and timing system 102. Delivery of pacing pulses to two or more heart chambers is controlled in part by the selection of programmable pacing intervals, which can include atrial-atrial (A-A), atrial-ventricular (A-V), and ventricular-ventricular (V-V) intervals.

Physiologic input signal processing circuit 108 is provided for receiving cardiac electrogram (EGM) signals for determining a patient's heart rhythm. Physiologic input signal processing circuit 108 additionally receives signals from left ventricular wall acceleration sensor 62, and RV wall acceleration sensor 60, and processes these signals and provides signal data to control and timing system 102 for further signal analysis. For purposes of illustration of the possible uses of the invention, a set of lead connections are depicted for making electrical connections between the therapy delivery system 106 and the input signal processing circuit 108 and sets of pace/sense electrodes, acceleration sensors, and any other physiological sensors located in operative relation to the RA, LA, RV and LV.

Control and timing system 102 controls the delivery of bi-atrial, bi-ventricular, or multi-chamber cardiac pacing pulses at selected intervals intended to improve heart chamber synchrony. The delivery of pacing pulses by IPG 14 may be provided according to programmable pacing intervals, such as programmable conduction delay window times as generally disclosed in U.S. Pat. No. 6,070,101 issued to Struble et al., incorporated herein by reference in its entirety, or programmable coupling intervals as generally disclosed in above-cited U.S. Pat. No. 6,473,645 issued to Levine. Selection of the programmable pacing intervals may be based on a determination of ventricular synchrony derived from LV wall motion sensor 62 and RV wall motion sensor 60 signals as will be described in greater detail below.

The therapy delivery system 106 can optionally be configured to include circuitry for delivering cardioversion/defibrillation therapy in addition to cardiac pacing pulses for controlling a patient's heart rhythm. Accordingly, leads in communication with the patient's heart could additionally include high-voltage cardioversion or defibrillation shock electrodes.

A battery 136 provides a source of electrical energy to power components and circuitry of IPG 14 and provide electrical stimulation energy for delivering electrical impulses to the heart. The typical energy source is a high energy density, low voltage battery 136 coupled with a power supply/POR circuit 126 having power-on-reset (POR) capability. The power supply/POR circuit 126 provides one or more low voltage power (Vlo), the POR signal, one or more reference voltage (VREF) sources, current sources, an elective replacement indicator (ERI) signal, and, in the case of a cardioversion/defibrillator capabilities, high voltage power (Vhi) to the therapy delivery system 106. Not all of the conventional interconnections of these voltages and signals are shown in FIG. 2.

Current electronic multi-chamber IPG circuitry typically employs clocked CMOS digital logic ICs that require a clock signal CLK provided by a piezoelectric crystal 132 and system clock 122 coupled thereto as well as discrete components, e.g., inductors, capacitors, transformers, high voltage protection diodes, and the like that are mounted with the ICs to one or more substrate or printed circuit board. In FIG. 2, each CLK signal generated by system clock 122 is routed to all applicable clocked logic via a clock tree. The system clock 122 provides one or more fixed frequency CLK signal that is independent of the battery voltage over an operating battery voltage range for system timing and control functions and in formatting uplink telemetry signal transmissions in the telemetry I/O circuit 124.

The RAM registers included in microprocessor-based control and timing system 102 may be used for storing data compiled from sensed EGM signals, acceleration signals, and/or relating to device operating history or other sensed physiologic parameters for uplink telemetry transmission upon receipt of a retrieval or interrogation instruction via a downlink telemetry transmission. Criteria for triggering data storage can be programmed via downlinked instructions and parameter values. Physiologic data, including acceleration data, may be stored on a triggered or periodic basis or by detection logic within the physiologic input signal processing circuit 108. In some cases, the IPG 14 includes a magnetic field sensitive switch 130 that closes in response to a magnetic field, and the closure causes a magnetic switch circuit 120 to issue a switch closed (SC) signal to control and timing system 102 which responds in a magnet mode. For example, the patient may be provided with a magnet 116 that can be applied over the subcutaneously implanted IPG 14 to close switch 130 and prompt the control and timing system to deliver a therapy and/or store physiologic data. Event related data, e.g., the date and time and current pacing parameters, may be stored along with the stored physiologic data for uplink telemetry in a later interrogation session.

Uplink and downlink telemetry capabilities are provided to enable communication with either a remotely located external medical device or a more proximal medical device on or in the patient's body. Stored EGM, or LV acceleration data as well as real-time generated physiologic data and non-physiologic data can be transmitted by uplink RF telemetry from the IPG 14 to the external programmer or other remote medical device 26 in response to a downlink telemetered interrogation command. As such, an antenna 128 is connected to radio frequency (RF) transceiver circuit 124 for the purposes of uplink/downlink telemetry operations. Telemetering both analog and digital data between antenna 128 and an external device 26, also equipped with an antenna 118, may be accomplished using numerous types of telemetry systems known in the art for use in implantable devices.

The physiologic input signal processing circuit 108 includes electrical signal amplifier circuits for amplifying, processing and sensing events from characteristics of the electrical sense signals or sensor output signals. The physiologic input signal processing circuit 108 may thus include a plurality of cardiac signal sense channels for sensing and processing cardiac signals from sense electrodes located in relation to a heart chamber. Each such channel typically includes a sense amplifier circuit for detecting specific cardiac events and an EGM amplifier circuit for providing an EGM signal to the control and timing system 102 for sampling, digitizing and storing or transmitting in an uplink transmission. Atrial and ventricular sense amplifiers include signal processing stages for detecting the occurrence of a P-wave or R-wave, respectively and providing an atrial sense or ventricular sense event signal to the control and timing system 102. Timing and control system 102 responds in accordance with its particular operating system to deliver or modify a pacing therapy, if appropriate, or to accumulate data for uplink telemetry transmission in a variety of ways known in the art. Thus the need for pacing pulse delivery is determined based on EGM signal input according to the particular operating mode in effect.

Input signal processing circuit 108 includes signal processing circuitry for receiving accelerometer or other wall motion sensor signals and may include amplifiers and filters for processing an analog accelerometer signal. Alternatively, accelerometer signals may be digitized and averaging and filtering of such signals may be performed by microcomputer 102 or other dedicated digital circuitry. Accelerometer signal processing circuitry is further provided for detection and/or determination of one or more acceleration signal characteristics such as maximum peak amplitude, slope, integral, threshold crossing or other time domain signal characteristic that may be used in deriving a ventricular synchrony metric as will be described below. Acceleration data from LV wall motion sensor 62 and RV wall motion sensor 60 are made available to control and timing system 102 via LV MOTION signal line and RV MOTION signal line, respectively, for determining a synchrony metric. The synchrony metric may further be used by control and timing system 102 for identifying pacing intervals producing optimal ventricular synchrony.

Figure 3:
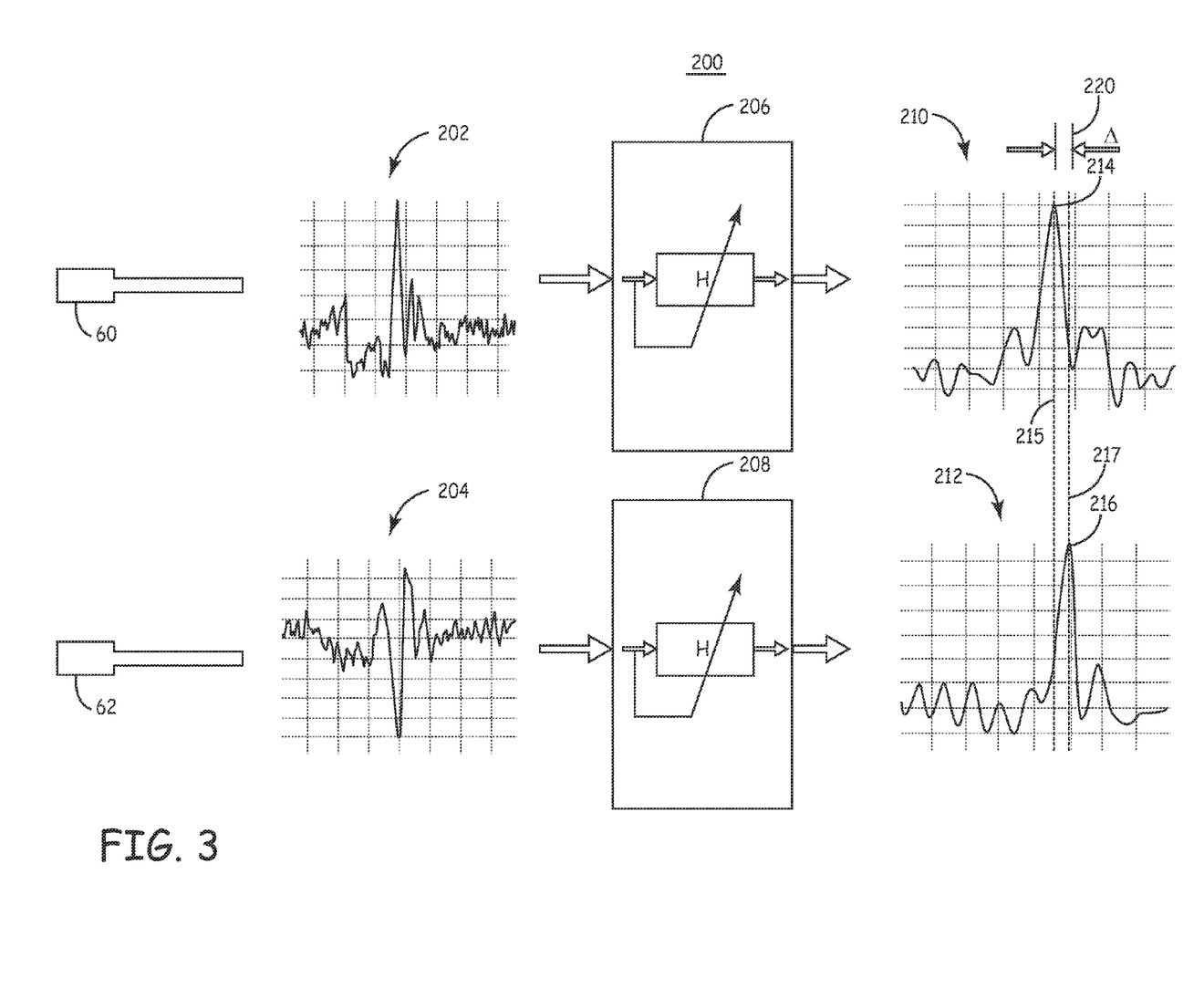
FIG. 3 is a schematic diagram summarizing steps included in a method for determining a metric of ventricular synchrony based on at least two accelerometer signals.

FIG. 3 is a schematic diagram summarizing steps included in a method for determining a metric of ventricular synchrony based on at least two accelerometer signals. A first raw accelerometer signal 202 is received from accelerometer 60, positioned to measure ventricular wall motion at a desired site, e.g., right ventricular wall motion as shown in FIG. 1. The raw accelerometer signal 202 is processed by processing unit 206 to produce a processed accelerometer signal 210. A fiducial point 214 on the processed signal 210 and the time point 215 at which it occurs is identified. The fiducial point 214 may be a peak amplitude as shown in FIG. 3 or alternatively any characteristic feature of the processed signal such as a peak slope or a threshold crossing.

In a similar method, a second raw accelerometer signal 204 is received from a second accelerometer 62 positioned at a second location for measuring ventricular wall motion, e.g. left ventricular free wall motion as shown in FIG. 1. The raw signal 204 is processed by processing unit 208 in the same manner as raw signal 202 to produce a processed signal 212. An analogous fiducial point 216 on processed signal 212 and the time point 217 at which it occurs are identified such that the time difference (A) 220 may be determined between the fiducial point 214 occurring on the first processed signal 210 and the analogous fiducial point 216 occurring on the second processed signal 212.

The time difference 220 between analogous fiducial points 214,216 provides a synchrony metric between the two ventricular sites at which the accelerometers 60 and 62 are located. In the example embodiment shown in FIG. 1, a measure of synchrony between right apical and left ventricular free wall motion may be obtained.

Figure 4:
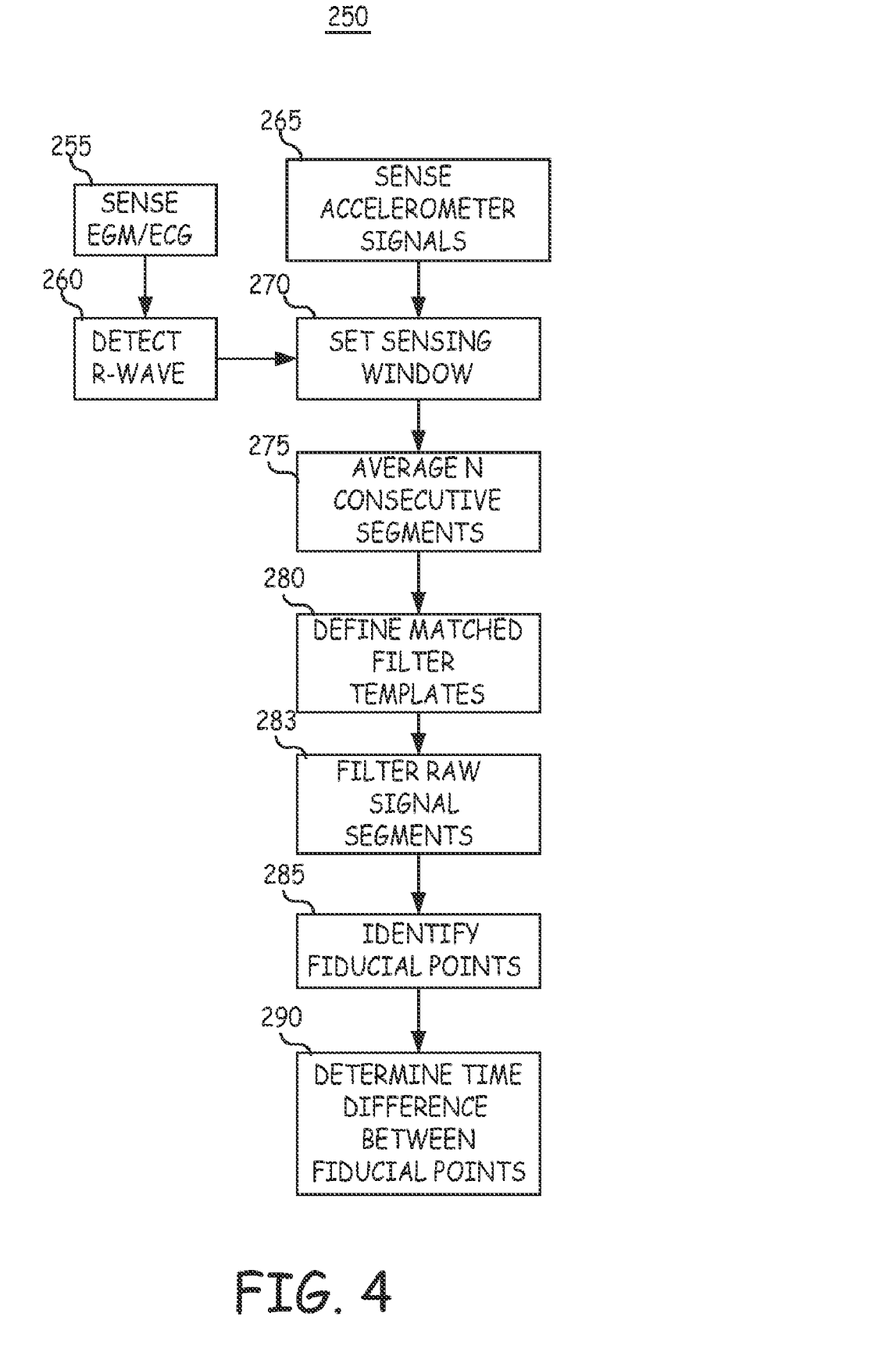
FIG. 4 is a flow chart summarizing steps included in a method for measuring ventricular synchrony as shown in FIG. 3 and providing additional details regarding the processing methods that may be used for converting a raw accelerometer signal into a processed signal useful for determining a synchrony metric.

FIG. 4 is a flow chart summarizing steps included in a method for measuring ventricular synchrony as shown in FIG. 3 and providing additional details regarding the processing methods that may be used for converting a raw accelerometer signal into a processed signal useful for determining a synchrony metric. An EGM or ECG signal is sensed at step 255 using transvenous or subcutaneous sensing electrodes such that the R-wave may be detected at step 260 for each cardiac cycle during a synchrony monitoring session. Any R-wave detection method may be used for the purposes of the present invention and such methods are well known in the art of cardiac pacing.

As described above, two or more accelerometers or other wall motion sensors are deployed at desired monitoring sites within the patient's heart. Simultaneously to EGM/ECG sensing, the two or more accelerometer signals are sensed at step 265. At step 270 a sensing window is set defining an accelerometer signal segment of interest within each cardiac cycle. The sensing window set at step 270 is preferably set for each cardiac cycle relative to the R-wave detected at step 265 for the same cardiac cycle. The sensing window may alternatively be set relative to other EGM/ECG events such as a T-wave or a P-wave or other atrial or ventricular senses or pace events. The sensing window is set so as to select a period during the cardiac cycle during which ventricular synchrony is to be evaluated. While the active ejection phase can be selected for evaluating ventricular synchrony, other phases may be of greater interest and value for extracting meaningful cardiac wall motion signals. In particular, the isovolumic contractile phase or the isovolumic relaxation phase appear to provide the most significant cardiac wall motion signals. However, other phases (e.g., the filling phase) can be use depending on the application of the synchrony metric.

Figure 5:
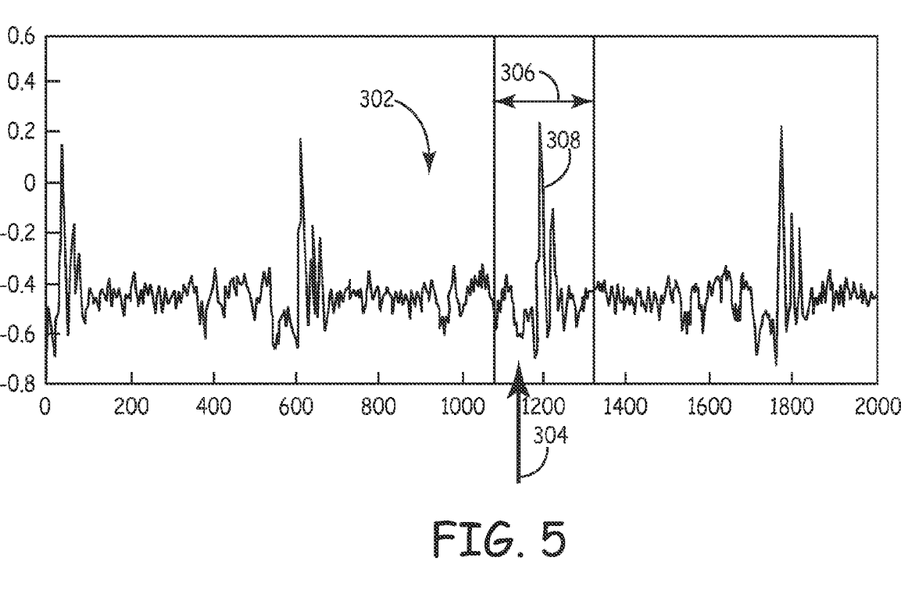
FIG. 5 is a sample recording of a raw accelerometer signal wherein a series of peaks are observed on the acceleration signal corresponding to the active ejection phase of each cardiac cycle.

In FIG. 5 a sample recording of a raw accelerometer signal is depicted wherein a series of peaks are observed on the acceleration signal corresponding to the active ejection phase of each cardiac cycle. An R-wave detected at a time point indicated by arrow 304 is used to set a sensing window 306, relative to R-wave detection time 304, for isolating the active ejection phase of the acceleration signal 302, during which a peak acceleration signal 308 is observed. The acceleration signal segment occurring during sensing window 306 will undergo further processing as described in the flow chart of FIG. 4 for determining a synchrony metric.

At step 275 of FIG. 4, a predetermined number of consecutive acceleration signal segments defined by the sensing window set at step 270 are averaged for a given accelerometer signal. Any number of one or more consecutive signal segments may be selected for averaging at step 275. At step 280, a template can be used for filtering the raw signal in a matched filter is defined. However, in lieu of a template, an appropriately configured conventional detection, also known as a matched filter, could be utilized. Presently, however, such matched filters are typically approximated by filters with far less numbers of coefficients and such approximated matched filters can also be used in practicing the present invention. The filter template, as will be described in greater detail below, is defined by reversing in time an averaged signal segment for a given accelerometer signal. A raw signal segment for each accelerometer signal may then be processed through a matched filter at step 283 using the filter template defined at step 280 for the corresponding accelerometer signal to improve the signal-to-noise ratio of the raw signal.

While other filtering methods may be performed, such as band pass filtering, matched filtering is preferred to achieve optimal signal-to-noise improvement. In performing matched filtering, the filter is designed to have a frequency response matching the frequency spectrum of the signal. The filter templates defined at step 283 therefore involves defining a filter template for each accelerometer signal received by reversing in time the averaged signal segment determined for each accelerometer signal.

A raw acceleration signal received at step 265 may be defined by Equation 1 below:

$$a(t)=A*s(t-tau)+n(t) \quad (1)$$

wherein a(t) is the raw acceleration signal including the acceleration signal contributions from noise, n(t), and ventricular wall motion defined by A*s(t−tau) wherein A is the strength of the myocardial acceleration and tau is the delay of the mechanical response of the myocardium following the electrical activation.

A filter template, h(t), may be defined according to Equation 2:

$$h(t)=\hat{s}(-t) \quad (2)$$

wherein $\hat{s}(-t)$ is the average of a predetermined number of signal segments determined at step 275 reversed in time.

After filtering each raw signal segment at step 283 using a matched filter employing the respective filter template defined by Equation 2 above, a processed signal for each raw accelerometer signal received is obtained as was described above in conjunction with FIG. 3. The signal to be filtered can comprise the raw signal segment obtained from a single cardiac cycle (and not the averaged signal segments found at step 275). In which case a a time difference is determined for a single cardiac cycle at step 285. Otherwise, a time difference can be determined for an averaged value of raw signals (over a plurality of cardiac cycles). Thus, the time difference for a single cardiac cycle or a plurality of cardiac cycles can calculated from the raw signals or from pre-filtered signals.

At step 285, the selected fiducial points are identified on each processed accelerometer signal. The time difference between these fiducial points is measured as a metric of synchrony at step 290 as described previously.

Figure 6:
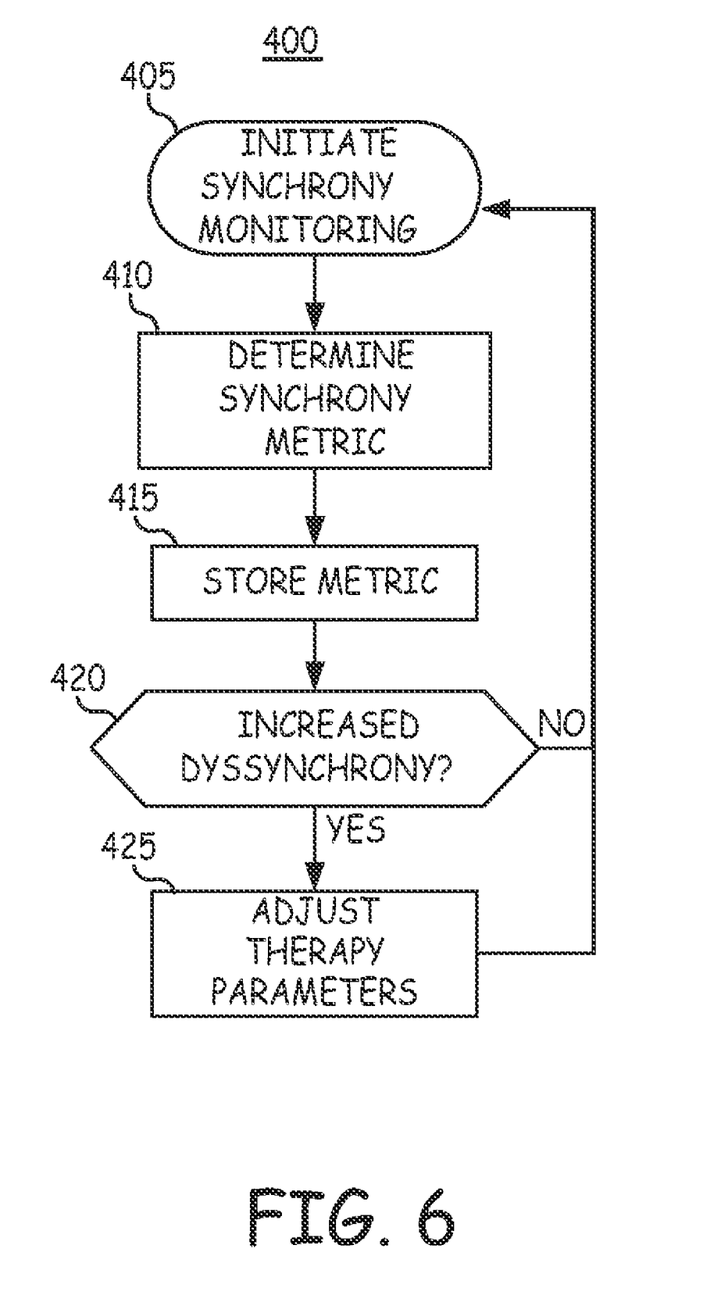
FIG. 6 is a flow chart summarizing steps included in a general method for monitoring ventricular synchrony and optionally adjusting a therapy based on a measurement of ventricular synchrony.

FIG. 6 is a flow chart summarizing steps included in a general method for monitoring ventricular synchrony and optionally adjusting a therapy based on a measurement of ventricular synchrony. At step 405 of method 400, synchrony monitoring is initiated. Monitoring of ventricular synchrony may be initiated by a user to occur on a continuous or periodic basis. For example, a synchrony metric may be determined on an hourly, daily, weekly or other periodic basis.

At step 410, a synchrony metric is determined from two or more accelerometers signals according to the methods described above in conjunction with FIGS. 3 through 5. The synchrony metric is stored at step 415 in associated device memory such that trends in ventricular synchrony may be recognized. Stored data is available for uplinking to an external device for display and review by a clinician.

The methods described herein for determining a metric of ventricular synchrony may be utilized for monitoring purposes only by the associated IMD. Therefore method 400 may include only the steps for determining and storing synchrony metrics. However, if the associated medical device includes therapy delivery capabilities, the stored synchrony metrics may be evaluated at step 420 to determine if a worsening trend in ventricular synchrony is indicated. If increased ventricular dyssynchrony is indicated, as determined at decision step 420, parameters used to control therapy delivery by the implantable device may be adjusted at step 425.

If the implantable device is a cardiac pacing device capable of dual chamber, bi-ventricular or multi-chamber pacing, the various A-V and V-V intervals used to control the timing of pacing pulses or other pacing control parameters may be adjusted at step 425 in an attempt to improve ventricular synchrony. If the implantable device is a drug delivery device, an adjustment may be made to the dosage of the delivered drug. After adjusting therapy parameters at step 425, method 400 may return to step 405 to initiate another measurement of ventricular synchrony to determine if the therapy parameter adjustment had the desired effect. If not, parameters may be adjusted until an improvement in ventricular synchrony is observed based on the trend of stored ventricular metrics. When no increase in ventricular dyssynchrony is indicated as determined at decision step 420, method 400 returns to step 405 to initiate synchrony monitoring at the next user-initiated or scheduled periodic monitoring time.

With respect to filtering of the raw sensor output signal(s), those of skill in the art of signal processing will appreciate that a matched filter can be approximated by a lower order filter using a variety of known techniques.

Thus a system and method for monitoring ventricular synchrony in ambulatory patients has been described which allows for chronic monitoring of ventricular synchrony and closed-loop control of therapies delivered by implantable devices to improve cardiac mechanics. The detailed embodiments described herein are intended to be illustrative, rather than limiting, with regard to the following claims.

What is claimed is:

1. A cardiac monitoring method, comprising:
deploying at least two cardiac wall motion sensors into operative communication with spaced-apart portions of myocardial tissue;

receiving a signal from each of the at least two cardiac wall motion sensors;
obtaining a sensor signal output segment for a predetermined sensing window for each of the at least two cardiac wall motion sensors;
filtering the sensor signal output segment of each of the at least two cardiac wall motion sensors;
locating an fiducial point for the filtered sensor signal output segments of each of the at least two cardiac wall motion sensors;
comparing the relative temporal location of the initial fiducial points of the filtered sensor signals of each of the at least two cardiac wall motion sensors; and
generating a metric of ventricular synchrony using the time difference between the relative temporal location of the initial fiducial points for each of the filtered sensor signal of the at least two cardiac wall motion sensors,
    wherein deploying one of the at least two cardiac wall motion sensors comprises deploying an accelerometer sensor.

2. A method according to claim 1 wherein deploying the accelerometer sensor comprises deploying a multiple axis accelerometer.

3. A method according to claim 1, further comprising:
programming a revised V-V interval based at least in part on the metric of ventricular synchrony.

4. A method according to claim 1, wherein the deploying step comprises deploying one of the at least two wall motion sensors to an epicardial location.

5. A method according to claim 1 wherein the step of obtaining a sensor signal segment for a predetermined sensing window for each of heat least two cardiac wall motion sensors, further comprises:
    initiating the predetermined sensing window beginning with a sensed cardiac event.

6. A method according to claim 5 wherein the sensed cardiac event comprises one of the group:
    a sensed P-wave, a sensed-Q wave, a sensed R-wave, a sensed T-wave, an atrial pacing stimulus, a ventricular pacing stimulus.

7. A method according to claim 1, wherein the step of locating an fiducial point for the filtered sensor signal output segments of each of the at least two cardiac wall motion sensors further comprises processing the output signal segments by one of:
    locating a maximum amplitude, locating a minimum amplitude, locating a maximum positive time derivative, locating a maximum negative time derivative, locating a threshold-crossing.

8. A method according to claim 7, Wherein locating the fiducial point comprises locating an initial occurrence of the fiducial point.

9. A cardiac monitoring method, comprising:
deploying at least two cerdiac wall motion sensors into operative communication with spaced-apart portions of myocardial tissue;
receiving a signal from each of the at least two cardiac wall motion sensors;
obtaining a sensor signal output segment for a predetermined sensing window for each of the at least two cadiac wall motion sensors;
filtering the sensor signal output segment of each of the at least two cardiac wall motion sensors;
locating an fiducial point for the filtered sensor signal output segments of each of the at least two cardiac wall motion sensors;
comparing the relative temporal location of the initial fiducial points of the filtered sensor signals of each of the at least two cardiac wall motion sensors; and
generating a metric of ventricular synchrony using the time difference between the relative temporal location of the initial fiducial points for each of the filtered sensor signal of the at least two cardiac wall motion sensors,
    wherein deploying one of the at least two cardiac wall motion sensors comprises deploying a tensiometric sensor.

10. A cardiac monitoring method, comprising:
deploying at least two cardiac wall motion sensors into operative communication with spaced-apart portions of myocardial tissue;
receiving a signal from each of the at least two cardiac wall motion sensors;
obtaining a sensor signal output segment for a predetermined sensing window for each of the at least two cardiac wall motion sensors;
filtering the sensor signal output segment of each of the at least two cardiac wall motion sensors;
locating an fiducial point for the filtered sensor signal output segments of each of the at least two cardiac wall motion sensors;
comparing the relative temporal location of the initial fiducial points of the filtered sensor signals of each of the at least two cardiac wall motion sensors; and
generating a metric of ventricular synchrony using the time difference between the relative temporal location of the initial fiducial points for each of the filtered sensor signal of the at least two cardiac wall motion sensors;
wherein the step of obtaining a sensor signal segment for a predetermined sensing window for each of the at least two cardiac wall motion sensors, further comprises:
initiating the predetermined sensing window upon one of the beginning or the expiration of a pacing therapy timing interval.

11. A method according to claim 10 wherein the pacing therapy timing interval comprises one of:
    an A-V interval, a V-A interval, a sensed A-V (SAV) interval, a paced A-V (PAV) interval, a post-ventricular atrial blanking (PVAB) interval, a post-ventricular atrial refractory period (PVARP).

12. A cardiac monitoring method, comprising:
deploying at least two cardiac wall motion sensors into operative communication with Spaced-apart portions of myocardial tissue;
receiving a signal from each of the at least two cardiac wall motion sensors;
obtaining a sensor signal output segment for a predetermined sensing window for each of the at least two cardiac wall motion sensors;
filtering the sensor signal output segment of each of the at least two cardiac wall motion sensors;
locating an fiducial point for the filtered sensor signal output segments of each of the at least two cardiac wall motion sensors;
comparing the relative temporal location of the initial fiducial points of the filtered sensor signals of each of the at least two cardiac wall motion sensors; and
generating a metric of ventricular synchrony using the time difference between the relative temporal location of the initial fiducial points for each of the filtered sensor signal of the at least two cardiac wall motion sensors, wherein the step of obtaining the sensor signal output segment for the predetermined sensing window for each of the at least two cardiac wall motion sensors comprises:

obtaining the sensor signal output segment over at least two cardiac cycles.

13. A method according to claim 12, wherein the at least two cardiac cycles comprise consecutive cardiac cycles.

14. A method according to claim 12, further comprising: averaging the sensor signal output segment.

15. A cardiac monitoring apparatus, comprising:

means for deploying at least two cardiac wall motion sensors into operative communication with spaced-apart portions of myocardial tissue;

means for receiving a signal from each of the at least two cardiac wall motion sensors;

means for obtaining a sensor signal output for a predetermined sensing window for each of the at least two cardiac wall motion sensors;

means for filtering the sensor signal output segment of each of the at least two cardiac wall motion sensors;

means for locating an fiducial point for the filtered sensor signal output segments of each of the at least two cardiac wall motion sensors;

means for comparing the relative temporal location of the initial fiducial points of the filtered sensor signals of each of the at least two cardiac wall motion sensors; and means for generating a metric of ventricular synchrony using the time difference between the relative temporal location of the initial fiducial points for each of the filtered sensor signal of the at least two cardiac wall motion sensors, wherein one of the at least two cardiac wall motion sensors comprises an accelerometer sensor.

16. An apparatus according to claim 15, wherein the accelerometer sensor comprises a multiple axis accelerometer.

17. An apparatus according to claim 15, wherein one of the at least two cardiac wall motion sensors comprises a tensiometric sensor.

18. An apparatus according to claim 15, wherein one of the at least two cardiac wall motion sensors comprises one of the group of: an acoustic sensor, a capacitive sensor, a strain gauge sensor, a piezoelectric-based sensor, an impedance-injection sensing circuit.

19. An apparatus according to claim 15, wherein the means for deploying comprises means for deploying one of the at least two wall motion sensors to an epicardial location.

20. An apparatus according to claim 15, wherein the means for obtaining a sensor signal segment for a predetermined sensing window for each of the at least two cardiac wall motion sensors, further comprises:

means for initiating the predetermined sensing window beginning with a sensed cardiac event.

21. An apparatus according to claim 20 wherein the sensed cardiac event comprises one of the group:

a sensed P-wave, a sensed-Q wave, a sensed R-wave, a sensed T-wave, an atrial pacing stimulus, a ventricular pacing stimulus.

22. An apparatus according to claim 15, wherein the means for obtaining a sensor signal segment for a predetermined sensing window for each of the at least two cardiac wall motion sensors, further comprises:

means for initiating the predetermined sensing window upon one of the beginning or the expiration of a pacing therapy timing interval.

23. An apparatus according to claim 22, wherein the pacing therapy timing interval comprises one of:

an A-V interval, a V-A interval, a sensed AN (SAV) interval, a paced A-V (PAV) interval, a post-ventricular atrial blanking (PVAB) interval, a post-ventricular atrial refractory period (PVARP).

24. An apparatus according to claim 15, wherein the means for locating an fiducial point for the filtered sensor signal output segments of each of the at least two cardiac wall motion sensors further comprises means for processing the output signal segments by one of:

means for locating a maximum amplitude, means for locating a minimum amplitude, means for locating a maximum positive time derivative, means for locating a maximum negative time derivative, means for locating a threshold-crossing.

25. An apparatus according to claim 24 wherein the means for locating the fiducial point comprises means for locating an initial occurrence of the fiducial point.

26. An apparatus according to claim 15, further comprising:

means for programming a revised V-V interval based at least in part on the metric of ventricular synchrony.

27. An apparatus according to claim 26 further comprising:

means for averaging the sensor signal output segment.

28. An apparatus according to claim 15, wherein the means for obtaining the sensor signal output segment for the predetermined sensing window for each of the at least two cardiac wall motion sensors comprises:

means for obtaining the sensor signal output segment over at least two cardiac cycles.

29. An apparatus according to claim 28, wherein the at least two cardiac cycles comprise consecutive cardiac cycles.

30. A computer readable mediums for performing a method of monitoring cardiac synchrony, comprising:

instructions for receiving a signal from each of the at least two cardiac wall motion sensors;

instructions for obtaining a sensor signal output segment for a predetermined sensing window for each of the at least two cardiac wall motion sensors;

instructions for filtering the sensor signal output segment of each of the at least two cardiac wall motion sensors;

instructions for locating an fiducial point for the filtered sensor signal output segments of each of the at least two cardiac wail motion sensors;

instructions for comparing the relative temporal location of the initial fiducial points of the filtered sensor signals of each of the at least two cardiac wall motion sensors; and instructions for generating a metric of ventricular synchrony using the time difference between the relative temporal location of the initial fiducial points for each of the filtered sensor signal of the at least two cardiac wall motion sensors, wherein the instructions for receiving the signal from one of the at least two cardiac wall motion sensors comprises instructions for receiving the signal from an accelerometer sensor.

31. A medium according to claim 30, wherein the instructions for receiving the signal from the accelerometer sensor comprises instructions for receiving the signal from a multiple axis accelerometer.

32. A medium according to claim 30, wherein the instructions for obtaining a sensor signal segment for a predetermined sensing window for each of the at least two cardiac wall motion sensors, further comprises:

instructions for initiating the predetermined sensing window beginning with a sensed cardiac event.

33. A medium according to claim 32, wherein the sensed cardiac event comprises one of the group:

a sensed P-wave, a sensed-Q wave, a sensed R-wave, a sensed T-wave, an atrial pacing stimulus, a ventricular pacing stimulus.

34. A medium according to claim 30, wherein the instructions for obtaining a sensor signal segment for a predetermined sensing window for each of the at least two cardiac wall motion sensors, further comprises:

instructions for initiating the predetermined sensing window upon one of the beginning or the expiration of a pacing therapy timing interval.

35. A medium according to claim 34, wherein the pacing therapy timing interval comprises one of:

an A-V interval, a V-A interval, a sensed A-V (SAV) interval, a paced A-V (PAV) interval, a post-ventricular atrial blanking (PVAB) interval, a post-ventricular atrial refractory period (PVARP).

36. A medium according to claim 30, wherein the instructions for locating an fiducial point for the filtered sensor signal output segments of each of the at least two cardiac wall motion sensors further comprises instructions for processing the output signal segments by one of:

instructions for locating a maximum amplitude, instructions for locating a minimum amplitude, instructions for locating a maximum positive time derivative, instructions for locating a maximum negative time derivative, instructions for locating a threshold-crossing.

37. A medium according to claim 36, wherein the instructions for locating the fiducial point comprises instructions for locating an initial occurrence of the fiducial point.

38. A medium according to claim 30, further comprising:

instructions for programming a revised V-V interval based at least in part on the metric of ventricular synchrony.

39. A medium according to claim 38, further comprising: averaging the sensor signal output segment.

40. A medium according to claim 30, wherein the instructions for obtaining the sensor signal output segment for the predetermined sensing window for each of the at least two cardiac wall motion sensors comprises:

instructions for obtaining the sensor signal output segment over at least two cardiac cycles.

41. A medium according to claim 40, wherein the at least two cardiac cycles comprise consecutive cardiac cycles.

42. A computer readable medium for performing a method of monitoring cardiac synchrony, comprising:

instructions for receiving a signal from each of the at least two cardiac wall motion sensors;

instructions for obtaining a sensor signal output segment for a predetermined sensing window for each of the at least two cardiac wall motion sensors;

instructions for filtering the sensor signal output segment of each of the at least two cardiac wall motion sensors;

instructions for locating an fiducial point for the filtered sensor signal output segments of each of the at least two cardiac wall motion sensors;

instructions for comparing the relative temporal location of the initial fiducial points of the filtered sensor signals of each of the at least two cardiac wall motion sensors; and instructions for generating a metric of ventricular synchrony using the time difference between the relative temporal location of the initial fiducial points for each of the filtered sensor signal of the at least two cardiac wall motion sensors, wherein the instructions for receiving the signal from one of the at least two cardiac wall motion sensors comprises instructions for receiving the signal from a tensiometric sensor.

* * * * *

UNITED STATES PATENT AND TRADEMARK OFFICE
CERTIFICATE OF CORRECTION

PATENT NO.       : 7,203,541 B2
APPLICATION NO.  : 10/799260
DATED            : April 10, 2007
INVENTOR(S)      : Sowelam et al.

It is certified that error appears in the above-identified patent and that said Letters Patent is hereby corrected as shown below:

Column 13, line 62 please change "two cadiac wall" to --two cardiac wall--.

Column 13, line 33 please change "of heat least" to --of the at least--.

Column 15, line 17 please change "output for" to --output segment for--.

Column 16, line 3 please change "a sensed AN(SAV)" to --a sensed A-V(SAV)--.

Column 16, line 48 please change "cardiac wail motion" to --cardiac wall motion--.

Signed and Sealed this

Second Day of October, 2007

JON W. DUDAS
*Director of the United States Patent and Trademark Office*